(12) United States Patent
Burley et al.

(10) Patent No.: US 10,582,935 B2
(45) Date of Patent: Mar. 10, 2020

(54) FLEXIBLE DRILL BIT

(71) Applicant: Stryker Puerto Rico Limited, Arroyo, PR (US)

(72) Inventors: J. Brook Burley, Mountain View, CA (US); Jeremy Graul, Elk Grove, CA (US); Sudip Pandya, Fremont, CA (US); James Flom, Redwood City, CA (US); Andrew Lantz, Redwood City, CA (US)

(73) Assignee: Stryker Puerto Rico Limited, PR (US)

( * ) Notice: Subject to any disclaimer, the term of this patent is extended or adjusted under 35 U.S.C. 154(b) by 357 days.

(21) Appl. No.: 13/735,806

(22) Filed: Jan. 7, 2013

(65) Prior Publication Data

US 2013/0261628 A1 Oct. 3, 2013

Related U.S. Application Data

(60) Provisional application No. 61/583,265, filed on Jan. 5, 2012.

(51) Int. Cl.
*A61B 17/16* (2006.01)
*A61B 17/17* (2006.01)

(52) U.S. Cl.
CPC ...... *A61B 17/1615* (2013.01); *A61B 17/1631* (2013.01); *A61B 17/17* (2013.01)

(58) Field of Classification Search
CPC ............ A61B 17/1615; A61B 17/1631; A61B 17/1633; A61B 17/1746; A61B 17/17; A61B 17/16; A61B 17/1622; A61B 17/1637
See application file for complete search history.

(56) References Cited

U.S. PATENT DOCUMENTS

| | | | |
|---|---|---|---|
| 4,541,423 A * | 9/1985 | Barber | 606/80 |
| 5,387,218 A | 2/1995 | Meswania | |
| 5,601,550 A | 2/1997 | Esser | |
| 5,733,290 A | 3/1998 | McCue et al. | |
| 6,309,396 B1 | 10/2001 | Ritland | |
| 6,422,010 B1 | 7/2002 | Julien | |
| 6,423,080 B1 | 7/2002 | Gellman et al. | |
| 2005/0054953 A1 | 3/2005 | Ryan et al. | |
| 2005/0059975 A1 | 3/2005 | Fanger et al. | |
| 2005/0203527 A1* | 9/2005 | Carrison | A61B 17/1604 606/80 |
| 2007/0264093 A1 | 11/2007 | White et al. | |
| 2008/0188854 A1 | 8/2008 | Moser | |
| 2008/0221620 A1 | 9/2008 | Krause | |

(Continued)

FOREIGN PATENT DOCUMENTS

| | | |
|---|---|---|
| EP | 1584299 | 10/2005 |
| WO | WO 2011/161676 | 12/2011 |
| WO | WO 2014/107729 | 7/2014 |

*Primary Examiner* — Si Ming Ku
(74) *Attorney, Agent, or Firm* — Pandiscio & Pandiscio

(57) ABSTRACT

A flexible drill bit including a proximal shaft portion for connecting to a source of turning; a distal cutting tip portion for boring into a material; and an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material.

40 Claims, 21 Drawing Sheets

(56) References Cited

U.S. PATENT DOCUMENTS

| | | | |
|---|---|---|---|
| 2009/0012526 A1* | 1/2009 | Fletcher | A61B 17/1615 606/96 |
| 2009/0149890 A1 | 6/2009 | Martin | |
| 2009/0204121 A1 | 8/2009 | Cavallazzi et al. | |
| 2010/0191248 A1 | 7/2010 | Mehta et al. | |
| 2010/0286694 A1 | 11/2010 | Rio et al. | |
| 2010/0292722 A1 | 11/2010 | Klaue | |
| 2011/0015674 A1 | 1/2011 | Howard et al. | |
| 2011/0071545 A1 | 3/2011 | Pamichev et al. | |
| 2011/0144703 A1 | 6/2011 | Krause et al. | |
| 2011/0208194 A1* | 8/2011 | Steiner | A61B 17/1631 606/80 |
| 2011/0251621 A1 | 10/2011 | Sluss et al. | |
| 2012/0123417 A1 | 5/2012 | Smith | |
| 2012/0203231 A1* | 8/2012 | Long | A61B 17/1631 606/80 |
| 2013/0158596 A1 | 6/2013 | Miller et al. | |
| 2014/0107657 A1 | 4/2014 | Norton et al. | |

\* cited by examiner

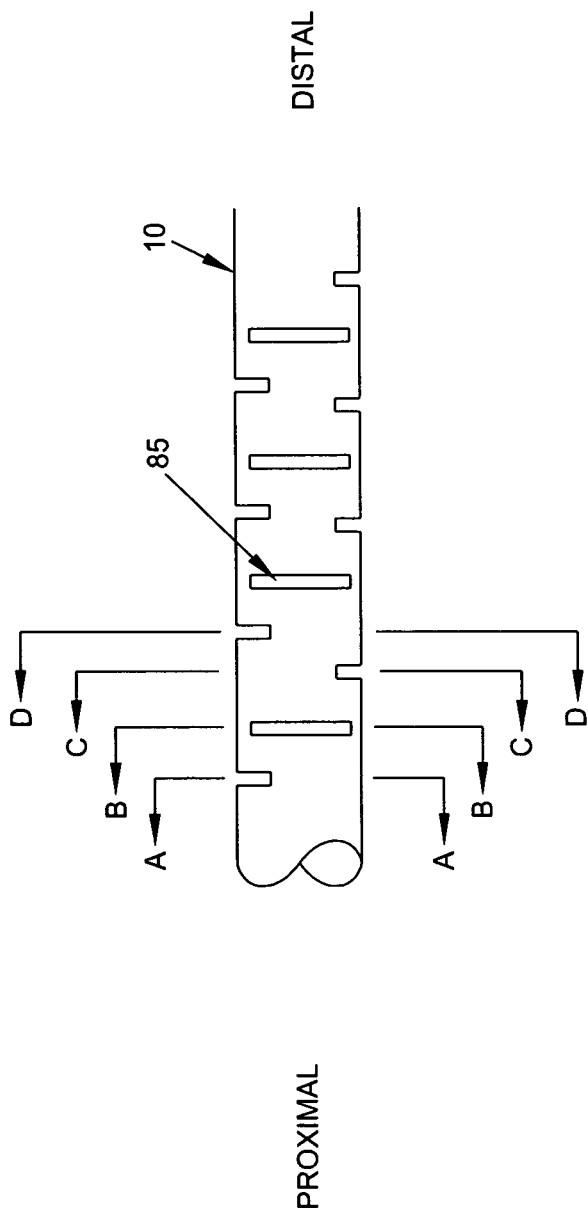
FIG. 15
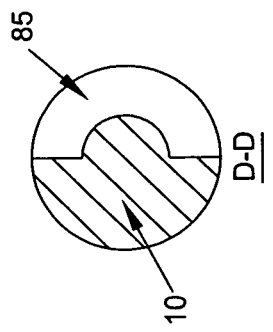
FIG. 19
FIG. 18
FIG. 17
FIG. 16

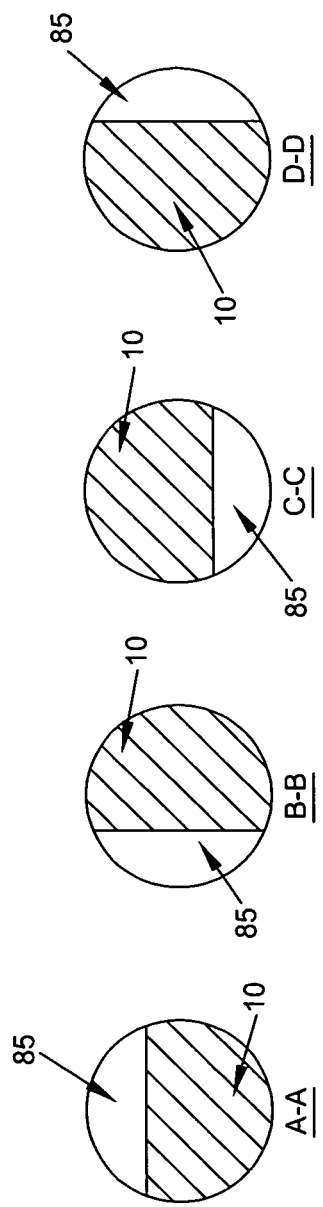

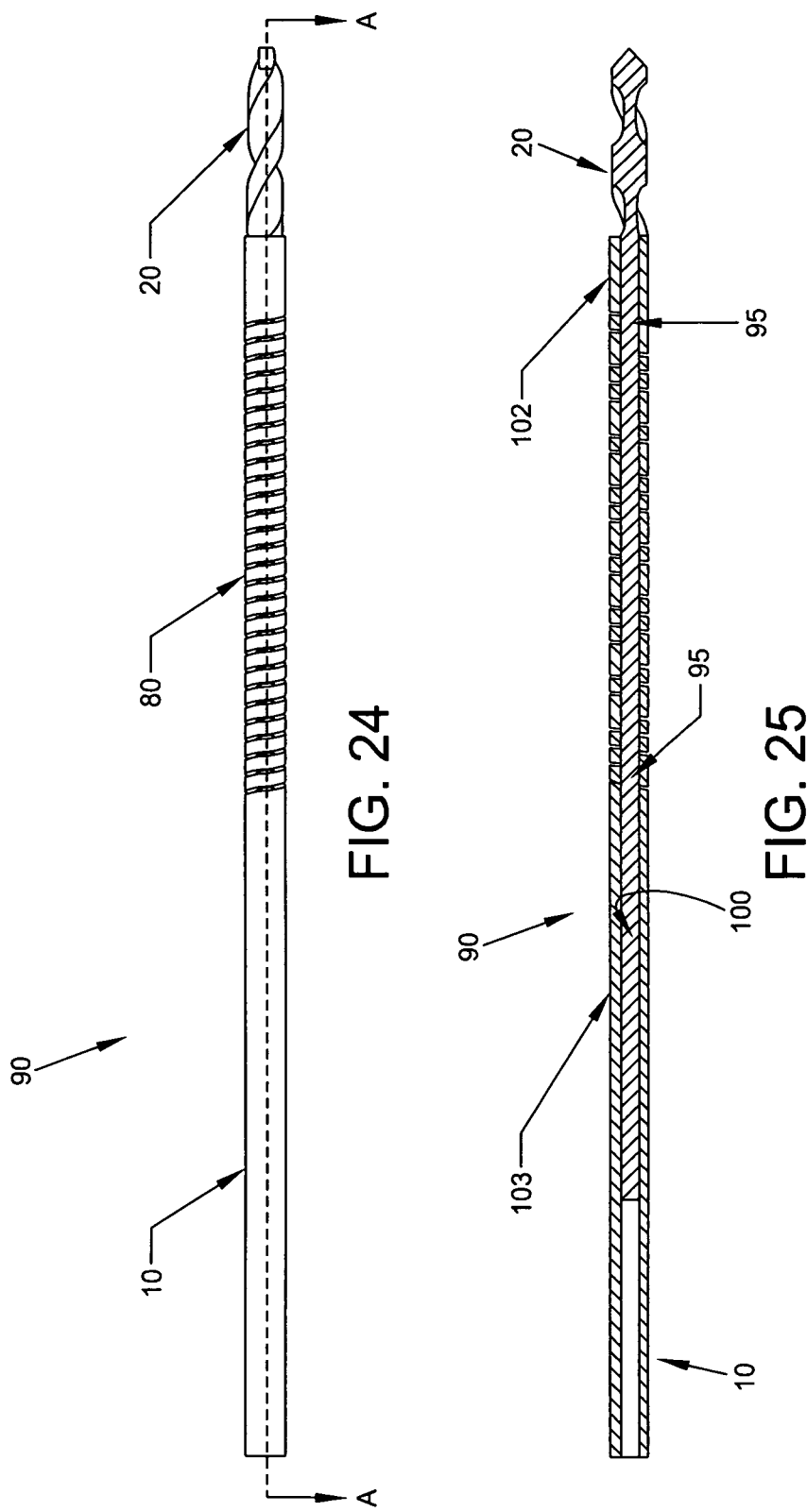

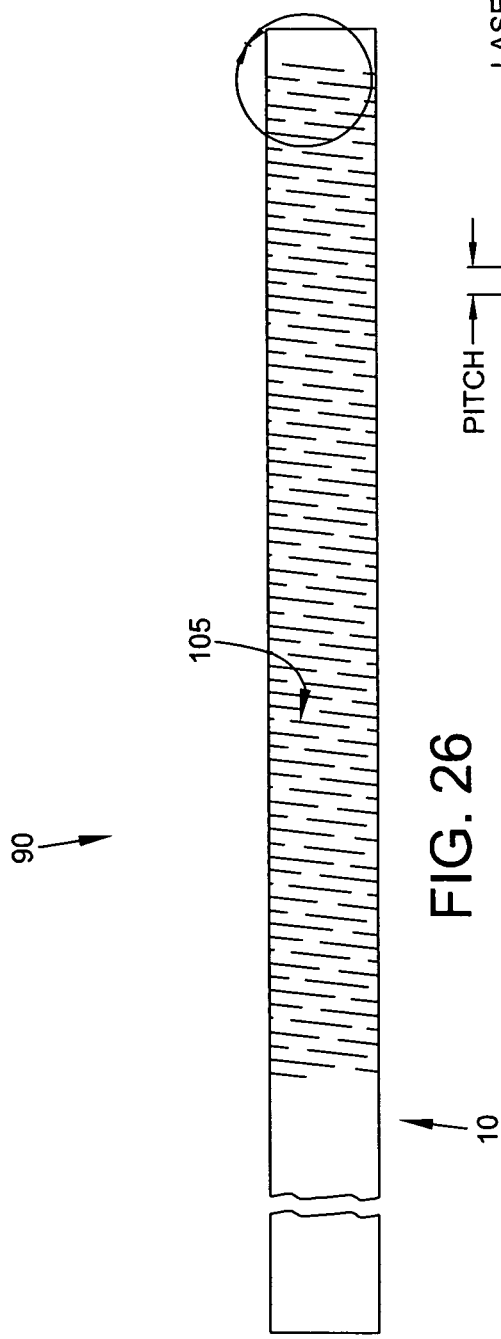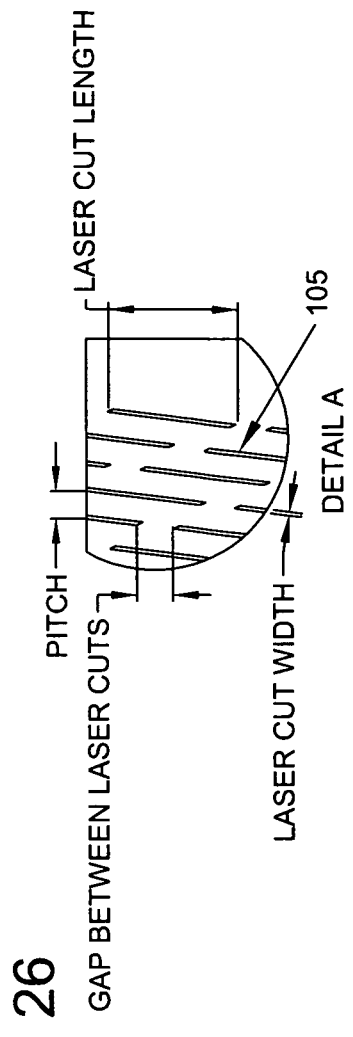

FLEXIBLE DRILL BIT

REFERENCE TO PENDING PRIOR PATENT APPLICATION

This patent application claims benefit of prior U.S. Provisional Patent Application Ser. No. 61/583,265, filed Jan. 5, 2012 by J. Brook Burley et al. for FLEXIBLE DRILL BIT, which patent application is hereby incorporated herein by reference.

FIELD OF THE INVENTION

This invention relates to surgical methods and apparatus in general, and more particularly to methods and apparatus for drilling a hole in bone.

BACKGROUND OF THE INVENTION

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is also common to repair torn meniscal cartilage in the knee joint, and/or to replace ruptured ACL ligaments in the knee joint, using minimally-invasive, keyhole techniques.

While such minimally-invasive approaches can require additional training on the part of the surgeon, such procedures generally offer substantial advantages for the patient and have now become standard procedures for treating many shoulder joint and knee joint pathologies.

In addition to the foregoing, in view of the inherent advantages and widespread availability of minimally-invasive approaches for treating pathologies of the shoulder joint and the knee joint, the current trend is to provide such treatment much earlier in the lifecycle of the pathology, so as to address patient pain and so as to reduce the likelihood of exacerbating the pathology itself. This is in marked contrast to traditional surgical practices, which generally dictated postponing surgical procedures for as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the complex geometry of the hip joint itself, and (ii) the nature and location of the pathologies which are typically encountered in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is generally relatively difficult for surgeons to perform minimally-invasive procedures on the hip joint.

Furthermore, the pathways and approaches for entering the interior of the hip joint (i.e., the natural pathways which exist between adjacent bones and/or delicate neurovascular structures) are generally much more limited for the hip joint than for the shoulder joint or the knee joint. This limited access further complicates a surgeon's ability to effectively perform minimally-invasive procedures on the hip joint.

In addition to the foregoing, the nature and location of the pathologies of the hip joint also complicate a surgeon's ability to perform minimally-invasive procedures on the hip joint. By way of example but not limitation, consider a typical labrum tear or detachment in the hip joint. In this situation, instruments must generally be introduced into the joint space at an angle of approach which is offset from the angle at which the instrument addresses the joint anatomy. This makes drilling into bone, for example, a significantly more complicated procedure than in a case where the angle of approach is effectively aligned with the angle at which the instrument addresses the joint anatomy, such as is frequently the case in the shoulder joint. Furthermore, since the working space within the hip joint is typically extremely limited, it is even more difficult to properly adjust the alignment of surgical instruments (e.g., a drill) where the angle of approach is not aligned with the optimal angle for the instrument to address the joint anatomy.

As a result of the foregoing, minimally-invasive hip joint procedures are still relatively difficult to perform and hence less common in practice. Consequently, patients are typically forced to manage and endure their hip pain for as long as possible, until a resurfacing procedure or a partial or total hip replacement procedure can no longer be avoided. These resurfacing or replacement procedures are generally then performed as a highly-invasive, open procedure, replete with all of the disadvantages associated with highly-invasive, open procedures.

As a result, there is, in general, a pressing need for improved methods and apparatus for treating pathologies of the hip joint.

More particularly, there is a pressing need for improved methods and apparatus for introducing instruments into the joint space where the instruments will address the joint anatomy at an angle which is offset from the angle of approach. By way of example but not limitation, in some cases it may be desirable to drill into bone at an angle which is offset from the angle at which the drill is inserted into the joint space, in order to create a hole in the bone at an optimum location, e.g., at an optimum location to receive a suture anchor for use in effecting a labral repair.

SUMMARY OF THE PRESENT INVENTION

These and other objects of the present invention are addressed by the provision and use of a new flexible drill bit, which may be used for drilling a hole in bone (or another material) where the flexible drill bit will enter the bone at an angle which is offset from the angle of approach.

The flexible drill bit is particularly advantageous in situations where it is desirable to pass the drill bit into a joint in a curved configuration, such as where the drill bit is to be inserted into the joint through a curved guide or cannula.

In accordance with the present invention, the flexible drill bit is constructed so that it is flexible enough to bend into a curved state, yet strong enough to transmit the torsional forces required for drilling into bone (or another material).

In one preferred form of the present invention, there is provided a flexible drill bit comprising:
 a proximal shaft portion for connecting to a source of turning;
 a distal cutting tip portion for boring into a material; and
 an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material.

In another preferred form of the present invention, there is provided a method for forming a hole in a material, the method comprising:
 providing a flexible drill bit comprising:
  a proximal shaft portion for connecting to a source of turning;
  a distal cutting tip portion for boring into a material; and
  an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material;
 advancing the flexible drill bit to the material along a first angle of approach;
 contacting the material at a second angle of approach; and
 turning the flexible drill bit so as to form a hole in the material.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 15 is a schematic view showing still another form of flexible drill bit formed in accordance with the present invention;

FIGS. 16-19 are schematic cross-sectional views taken along lines A-A, B-B, C-C and D-D, respectively, of FIG. 15 in one form of the invention;

FIGS. 20-23 are schematic cross-sectional views taken along lines A-A, B-B, C-C and D-D, respectively, of FIG. 15 in another form of the invention;

FIG. 24 is a schematic view showing another form of flexible drill bit formed in accordance with the present invention;

FIG. 25 is a schematic cross-sectional view taken along line A-A of FIG. 24;

FIG. 26 is a schematic view showing still another form of flexible drill bit formed in accordance with the present invention;

FIG. 27 is an enlarged schematic view showing selected portions of the flexible drill bit of FIG. 26.

DETAILED DESCRIPTION OF THE PREFERRED EMBODIMENTS

Flexible Drill Bit Having a "Unibody" Construction

Figure 1:
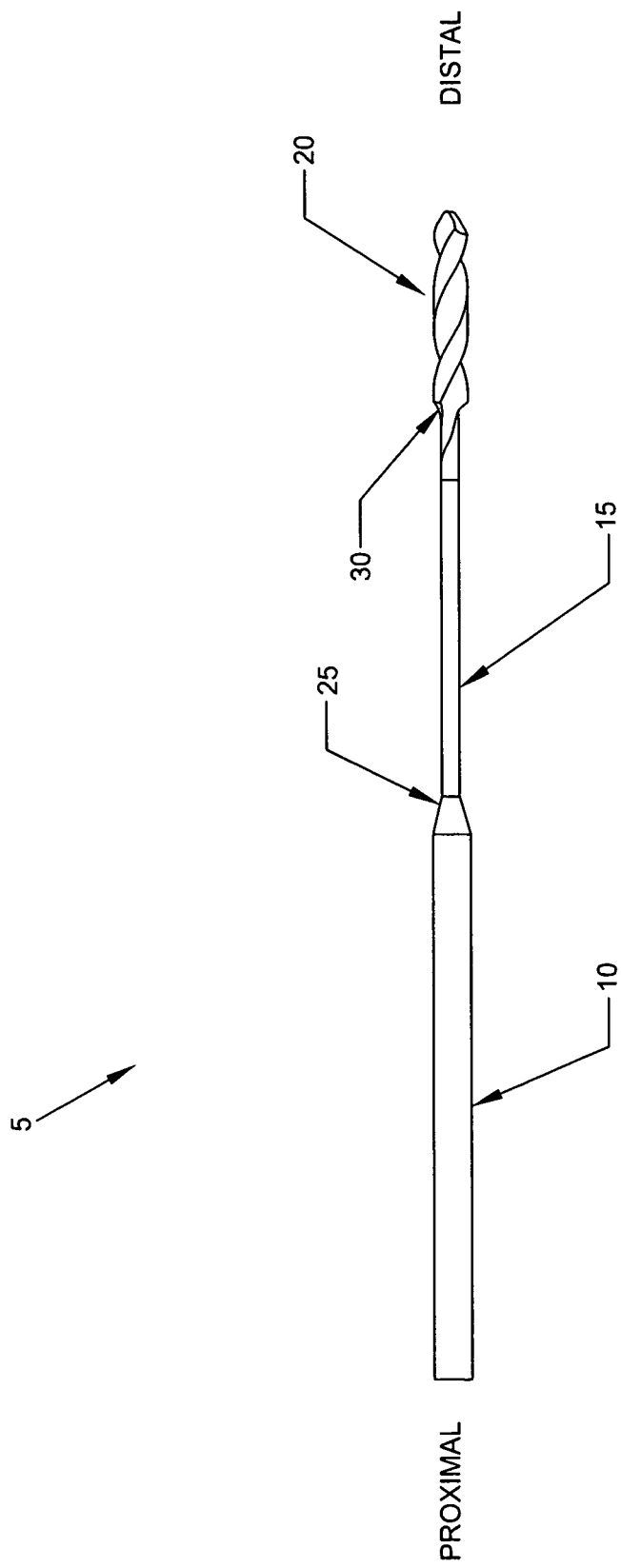
FIG. 1 is a schematic view showing a flexible drill bit formed in accordance with the present invention.
Figure 2:
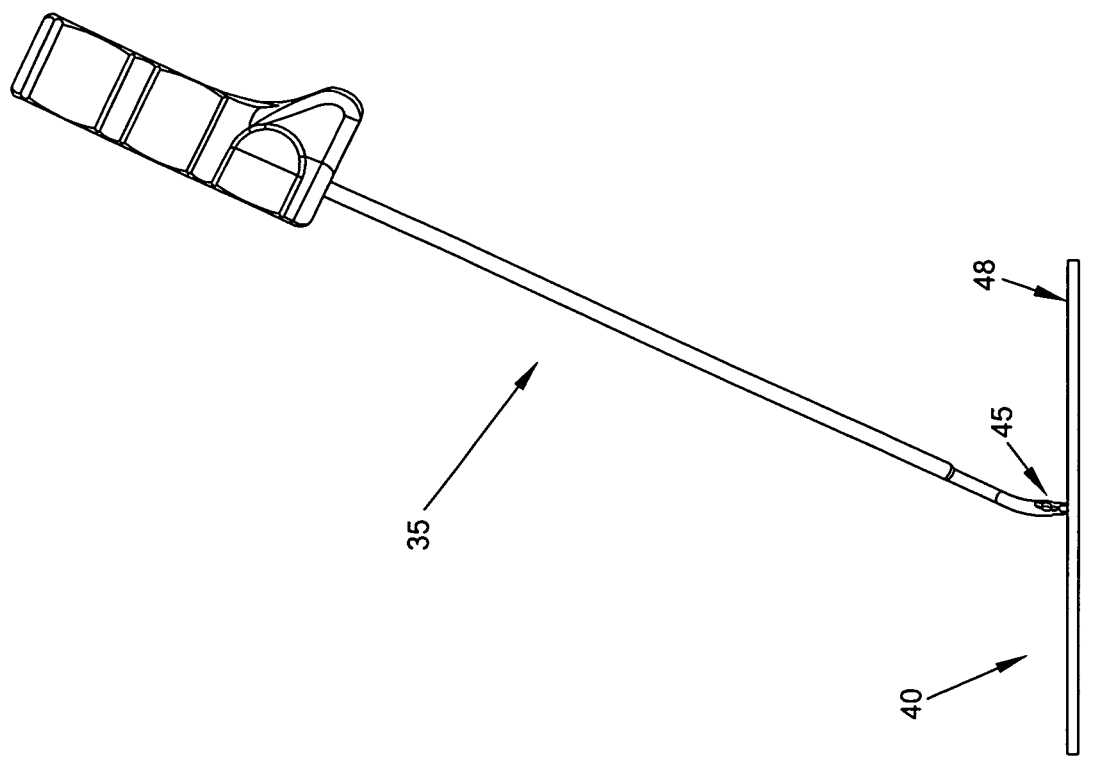
FIGS. 2-5 are schematic views showing the flexible drill bit of FIG. 1 being used in conjunction with a curved drill guide to form a hole in bone.
Figure 3:
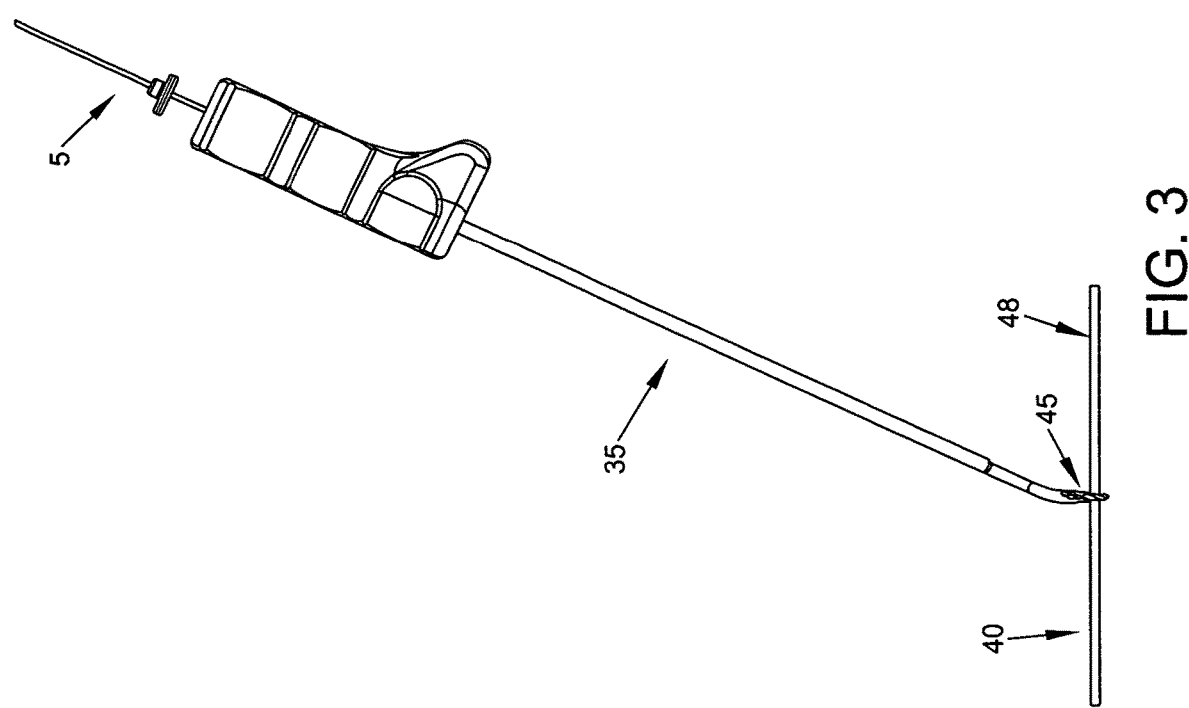
Figure 4:
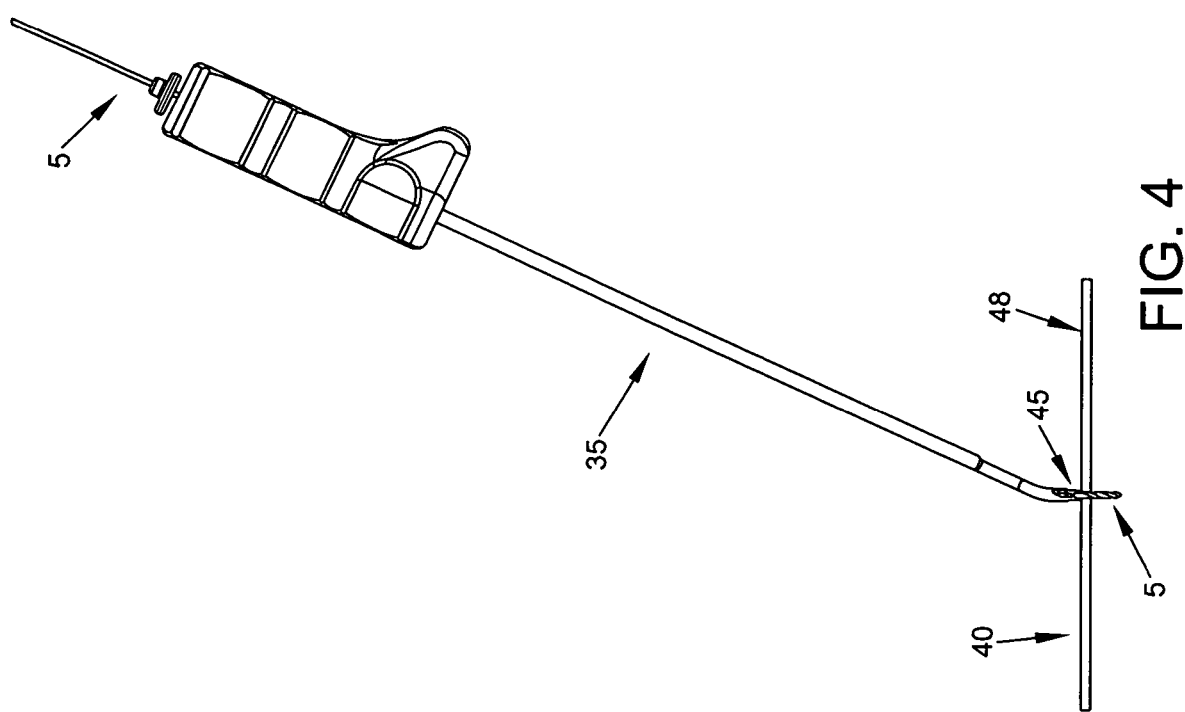

Looking first at FIG. 1, there is a shown a flexible drill bit 5 formed in accordance with the present invention. Flexible drill bit 5 comprises three sections, i.e., a full diameter shaft portion 10, a reduced diameter shaft portion 15, and a fluted cutting tip portion 20. Full diameter shaft portion 10, reduced diameter shaft portion 15, and fluted cutting tip portion 20 are all formed integral with one another so as to create a flexible drill bit having a "unibody" construction. If desired, a transition area 25 may be formed between full diameter shaft portion 10 and reduced diameter shaft portion 15, and/or a transition area 30 may be formed between reduced diameter shaft portion 15 and fluted cutting tip portion 20.

The "unibody" construction eliminates the need for a mechanical joint connecting the cutting tip of the flexible drill bit (e.g., fluted cutting tip portion 20) to the flexible portion of the flexible drill bit (e.g., reduced diameter shaft portion 15), thereby eliminating a possible point of failure. Such a failure of a mechanical joint can be particularly problematic if the mechanical joint were to fail below the surface of the bone (i.e., subchondral); in this scenario, it would be unlikely that the portion of the drill bit left in the bone could be recovered. Thus, the possible failure of such a mechanical joint creates a serious clinical concern. In addition, the "unibody" construction eliminates the need for a mechanical joint connecting the flexible portion of the flexible drill bit (e.g., reduced diameter shaft portion 15) to the full diameter shaft portion (e.g., full diameter shaft portion 10) of the flexible drill bit, thus eliminating another possible point of failure.

The flexible drill bit may comprise a material such as Nitinol, stainless steel, titanium, or other appropriate material, but is preferably Nitinol.

The reduced diameter shaft portion 15 of flexible drill bit 5 provides flexibility in that portion of the drill bit while still providing the torsional strength needed to drill into bone. The diameter of the reduced diameter shaft portion 15 is preferably approximately 20-40% smaller than the diameter of the full diameter shaft portion 10, and more preferably approximately 25% smaller than the diameter of the full diameter shaft portion 10.

The transition area 30 located between fluted cutting tip portion 20 and the reduced diameter shaft portion 15, and/or the transition area 25 located between the reduced diameter shaft portion 15 and the full diameter shaft portion 10, are preferably formed so as to distribute stress, whereby to minimize the possibility of mechanical failure at the transition areas.

Full diameter shaft portion 10 provides a region, preferably at its proximal end, in which flexible drill bit 5 can be attached to a drill.

Fluted cutting tip portion 20 is preferably sufficiently rigid to form a straight hole in the target bone. To that end, the length of fluted cutting tip portion 20 must be short enough so that the fluted cutting tip portion 20 may pass through the curve of a curved drill guide or curved cannula. In one preferred embodiment, fluted cutting tip portion 20 has a length which is approximately 6 times greater than its diameter.

FIGS. 2-5 show flexible drill bit 5 being used in conjunction with a curved drill guide 35 to form a hole in a bone 40. More particularly, as seen in the figures, the distal tip 45 of curved drill guide 35 is placed against the outer surface 48 of bone 40, and then flexible drill bit 5 is passed through the lumen 50 of curved drill guide 35 and directed into bone 40 so as to make the hole in the bone at the desired location and with the desired angle.

Figure 5:
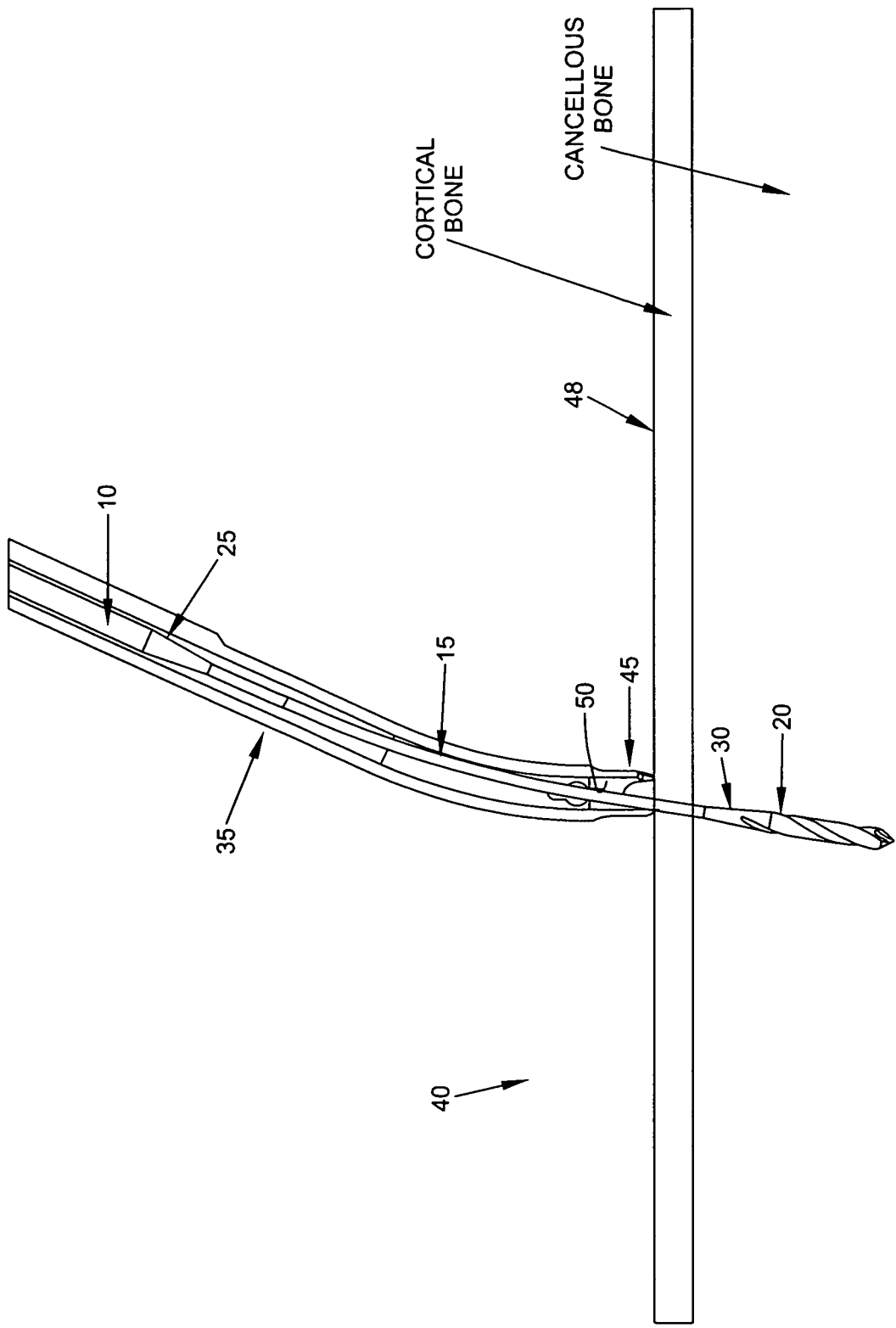

Note in FIG. 5 how the curvature of curved drill guide 35 can combine with the differences in the diameters of the reduced diameter shaft portion 15 and lumen 50 so as to result in a non-perpendicular entry of flexible drill bit 5 into the bone, even where distal tip 45 of curved drill guide 35 is disposed substantially perpendicular to outer surface 48 of the bone. In other words, the curvature of curved drill guide 35 can combine with the differences in the diameters of reduced diameter shaft portion 15 and lumen 50 so that fluted cutting tip portion 20 is not perfectly coaxial with lumen 50 as fluted cutting tip portion 20 emerges from the distal end of curved drill guide 35. It will be apparent to one skilled in the art that, depending on the bone surface contour and/or the angle of approach of curved drill guide 35, the curved drill guide 35 may not always be disposed perpendicular to outer surface 48 of the bone. In this scenario, it is typically still desirable to have the fluted cutting tip portion 20 centered and aligned with the end of the curved drill guide 35.

Figure 6:
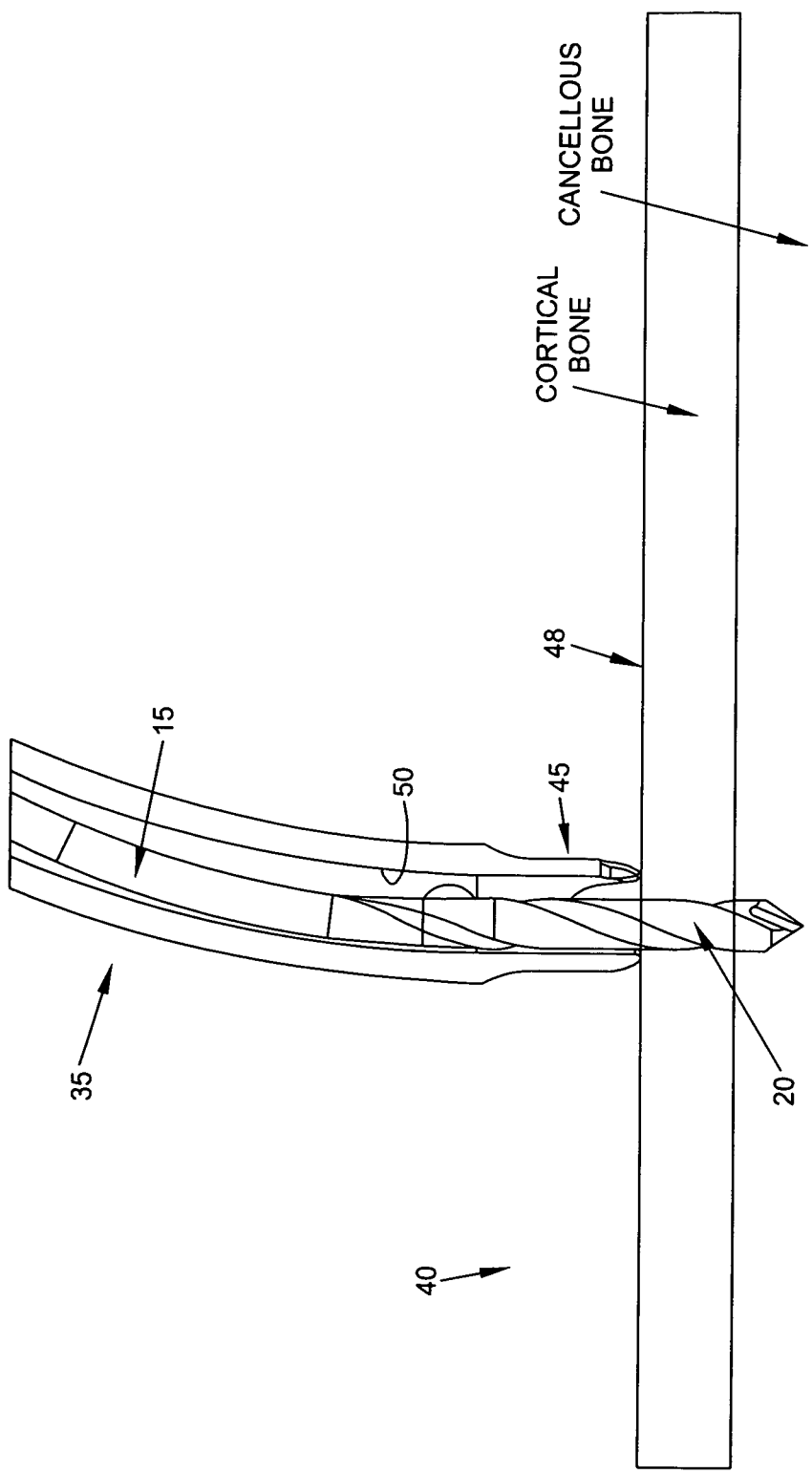
FIGS. 6 and 7 are schematic views showing another flexible drill bit formed in accordance with the present invention and being used in conjunction with a curved drill guide to form a hole in bone.
Figure 7:
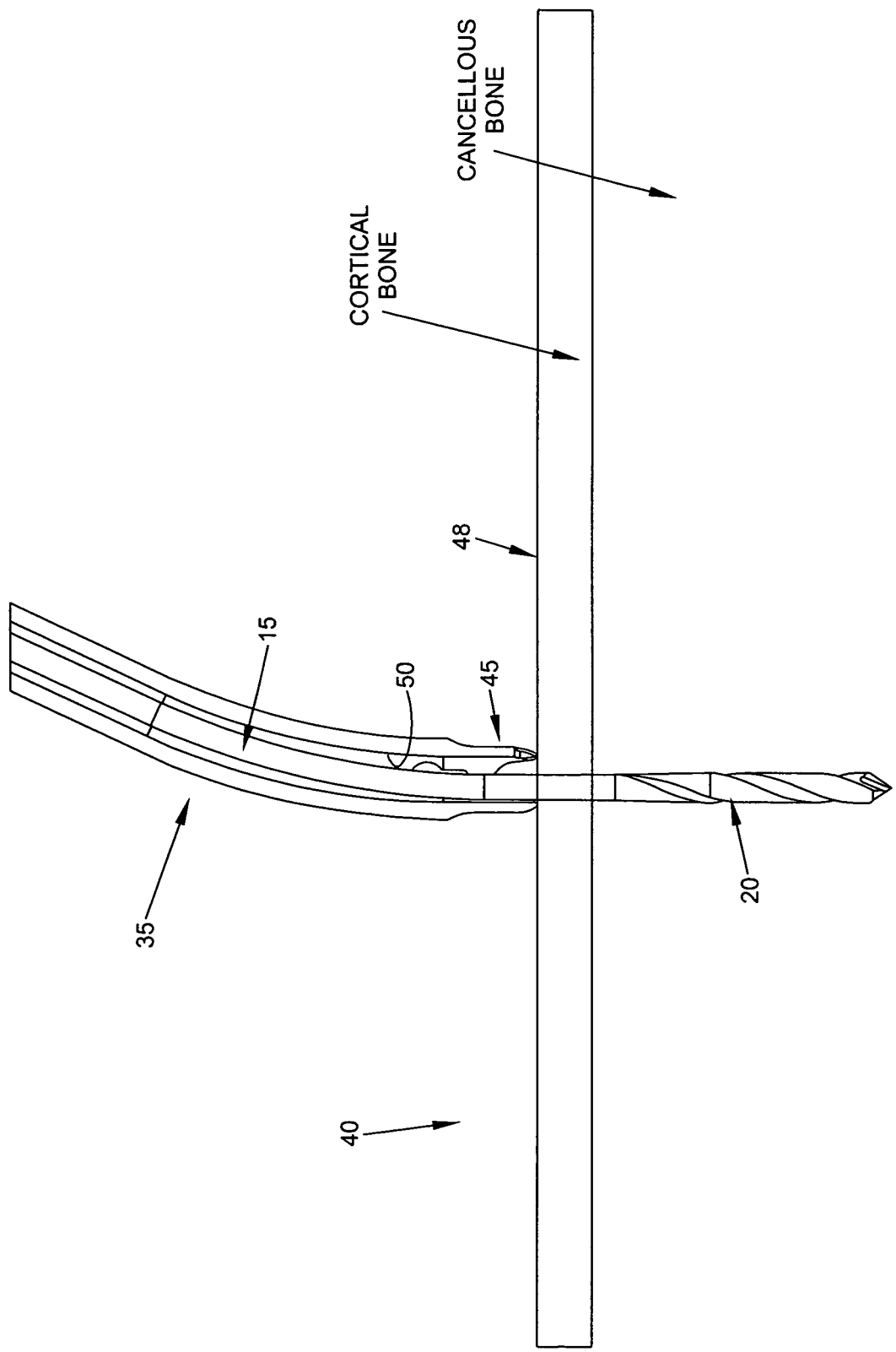

FIGS. 6 and 7 show another form of the invention where the diameter of reduced diameter shaft portion 15 is sized so as to be closer to the diameter of fluted cutting tip portion 20 and so as to be somewhat closer to the diameter of lumen 50 of curved drill guide 35. In this form of the invention, flexible drill bit 5 will tend to enter the bone closer to perpendicular. In other words, in this form of the invention, fluted cutting tip portion 20 will tend to remain more coaxial with lumen 50 as fluted cutting tip portion 20 emerges from the distal end of curved drill guide 35.

In one preferred form of the invention, full diameter shaft portion 10 has a length of approximately 12 inches and a diameter of approximately 0.063 inch; reduced diameter shaft portion 15 has a length of approximately 1.5 inches and a diameter of approximately 0.047 inch; fluted cutting tip portion 20 has a length of approximately 0.325 inch and a diameter of approximately 0.055 inch; and curved drill guide 35 has a radius of curvature of approximately 1.25 inches, a curve of approximately 25 degrees, and a lumen diameter of approximately 0.071 inch. In this preferred form of the invention, flexible drill bit 5 is capable of transmitting at least approximately 2 in-lbs (inch-pounds) of torque without failure, and more preferably approximately 3 in-lbs (inch-pounds) of torque without failure.

Figure 8:
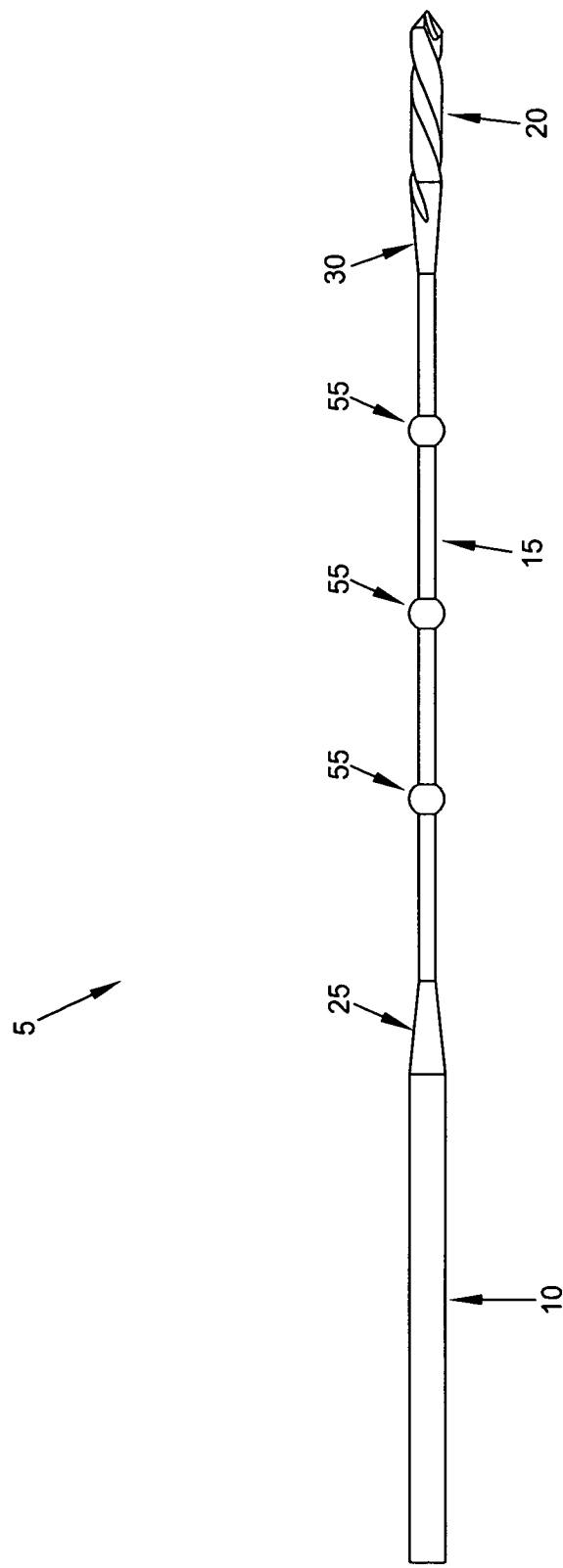
FIG. 8 is a schematic view showing still another flexible drill bit formed in accordance with the present invention.
Figure 9:
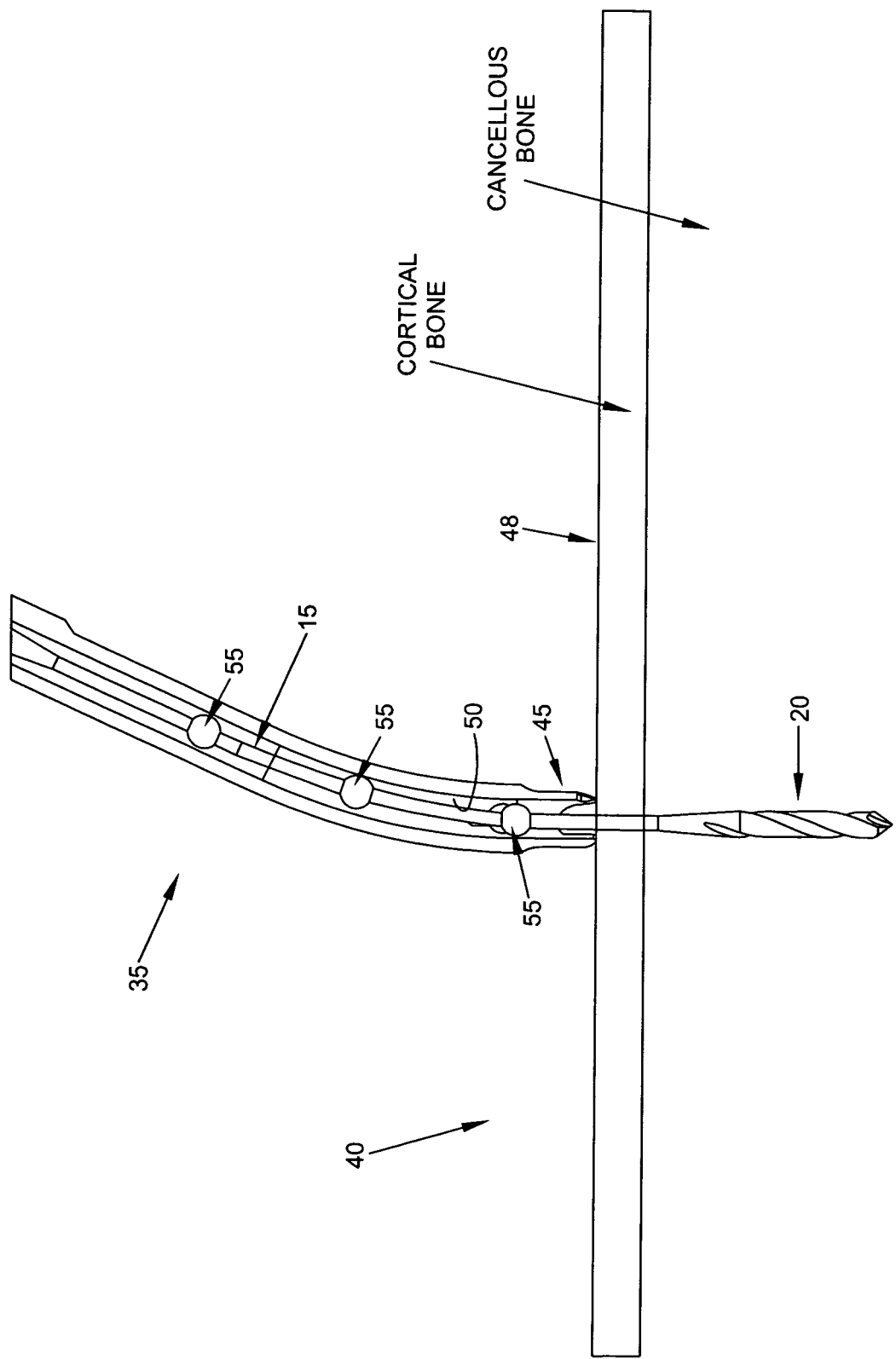
FIG. 9 is a schematic view showing the flexible drill bit of FIG. 8 being used in conjunction with a curved drill guide to form a hole in bone.

In another form of the invention, and looking now at FIGS. 8 and 9, one or more enlargements 55 may be formed on the reduced diameter shaft portion 15 of flexible drill bit 5. Enlargements 55 serve to keep flexible drill bit 5 centered in lumen 50 of curved drill guide 35 even where reduced diameter shaft portion 15 has a diameter which is significantly less than the diameter of lumen 50 of curved drill guide 35. In this form of the invention, enlargements 55 will also keep flexible drill bit 5 closer to perpendicular as it enters bone 40. In other words, in this form of the invention, fluted cutting tip portion 20 will tend to remain more coaxial with lumen 50 as fluted cutting tip portion 20 emerges from the distal end of curved drill guide 35.

Figure 10:
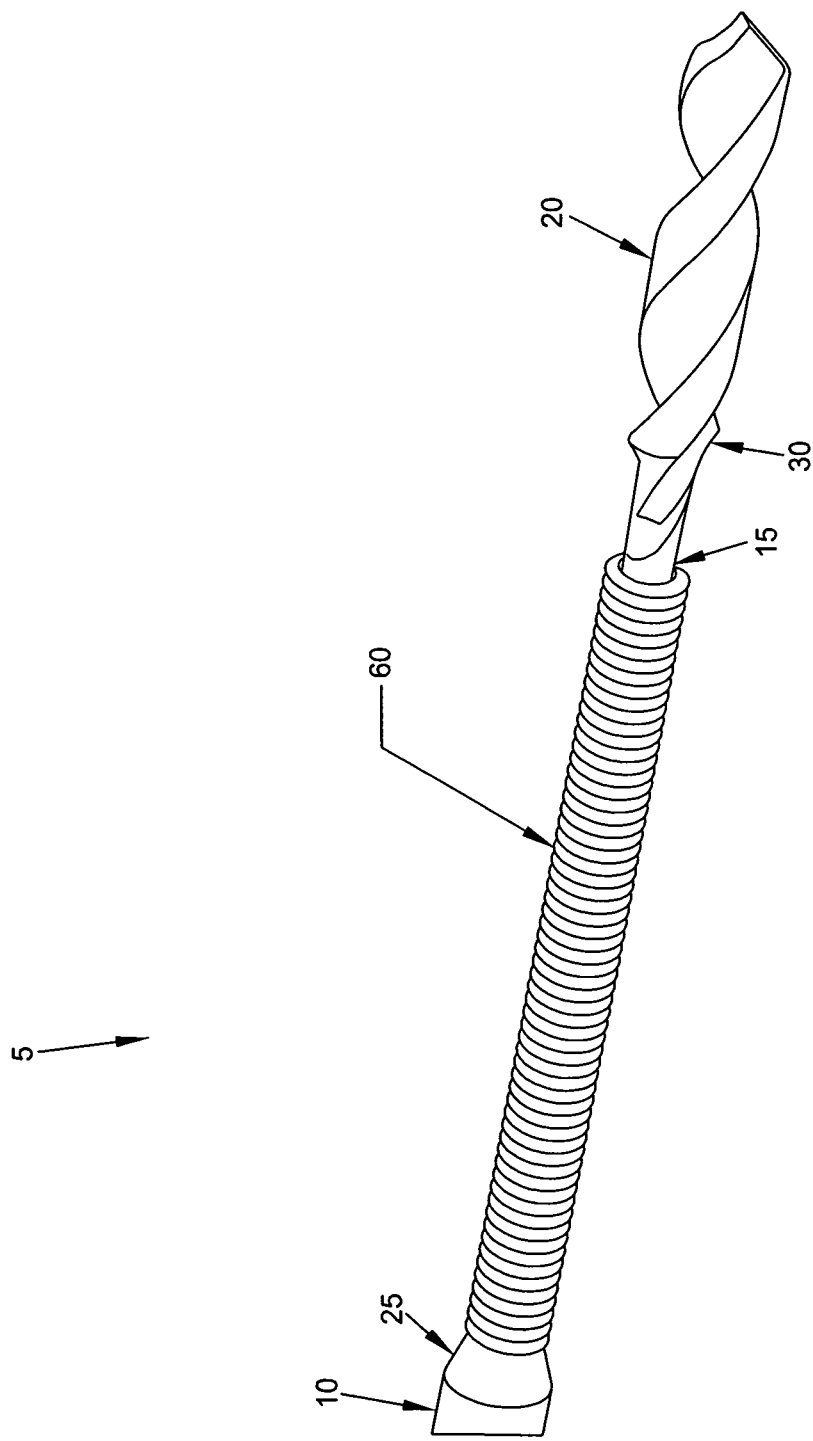
FIG. 10 is a schematic view showing the flexible drill bit of FIG. 1 with a helical coil disposed over a portion of the flexible drill bit.

In another embodiment, and looking now at FIG. 10, a helical coil 60 may be positioned over reduced diameter shaft portion 15 of flexible drill bit 5 so as to supplement the torque needed to drill into bone while still providing the flexibility needed to maneuver around a curve in a curved drill guide (e.g., curved drill guide 35) or curved cannula. Helical coil 60 also helps to keep flexible drill bit 5 centered in a curved drill guide (e.g., curved drill guide 35) and reduce the "mismatch" angle between flexible drill bit 5 and end of curved drill guide 35.

More particularly, helical coil 60 provides additional torsional strength and increased diameter to the reduced diameter shaft portion 15 of flexible drill bit 5 without significantly reducing the flexibility of the drill bit. The increased diameter of reduced diameter shaft portion 15 of flexible drill bit 5 (due to the presence of helical coil 60) creates a close fit within the drill guide or cannula, thereby ensuring that the drill bit remains coaxial with the curved drill guide or curved cannula as the flexible drill bit emerges from the distal end of the curved drill guide or curved cannula and engages the bone (or other material) which is being drilled.

Helical coil 60 may form a close fit around reduced diameter shaft portion 15 and be sized so that it rests between transition area 25 and transition area 30. Helical coil 60 may be resilient and may be stretched slightly (in its diameter) from its unbiased condition so as to allow the helical coil to be positioned onto reduced diameter shaft portion 15; in other words, in a free condition, the helical coil 60 has an inner diameter which is smaller than the outer diameter of the reduced diameter shaft portion 15. Helical coil 60 may simply sit on reduced diameter shaft portion 15, or it may be secured to reduced diameter shaft portion 15 (e.g., at one end of helical coil 60, at both ends of helical coil 60, and/or intermediate helical coil 60, etc.). In one preferred embodiment, helical coil 60 is secured at both its ends to reduced diameter shaft portion 15 and forms a close fit with reduced diameter shaft portion 15 or is stretched slightly diametrically from its unbiased condition onto reduced diameter shaft portion 15. Helical coil 60 may be secured to reduced diameter shaft portion 15 by soldering, adhesive, welding, mechanical interlock, or other appropriate attachment means. Helical coil 60 is preferably formed and positioned so that when the flexible drill bit is used to drill into bone, the helical coil will tighten onto reduced diameter shaft portion 15 during drilling. For example, if a flexible drill bit 5 rotates in a clockwise direction (when viewed from proximal to distal), the helical coil should have a counter-clockwise winding direction (again, when viewed from proximal to distal). This arrangement provides a preferred transfer of torque between reduced diameter shaft portion 15 and helical coil 60.

Helical coil 60 may comprise a material such as stainless steel, Nitinol or other suitable material. Helical coil 60 may comprise a wire of round or rectangular cross-section. Although FIG. 10 depicts a closely wound helical coil (i.e., with substantially no space between the coils), an alternative embodiment comprises spacing between the coils.

Figure 11:
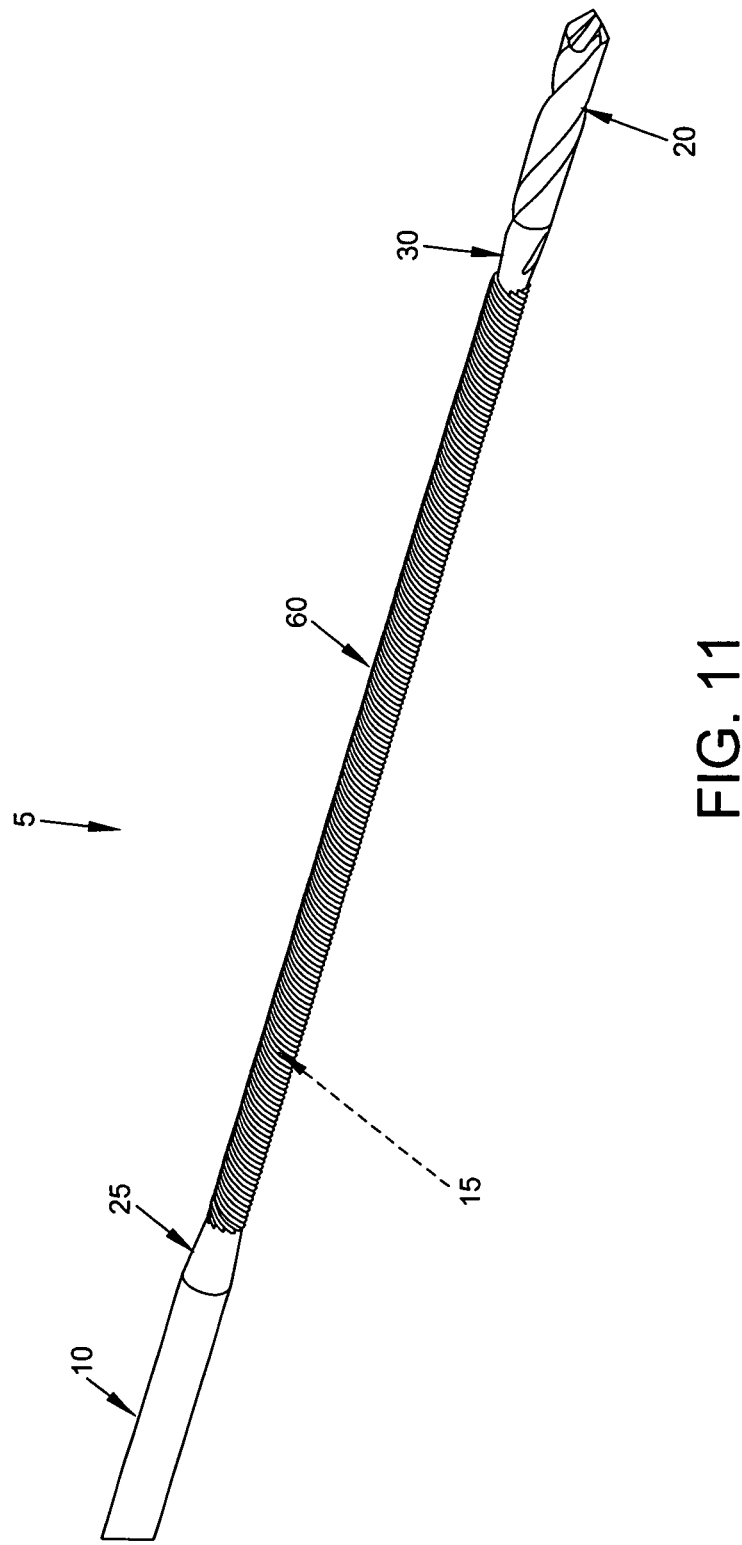
FIG. 11 is a schematic view showing the flexible drill bit of FIG. 1 with another form of helical coil disposed over a portion of the flexible drill bit.

FIG. 11 shows a construction similar to that of FIG. 10, except that helical coil 60 comprises a multi-strand coil (i.e., multiple strands are coiled together). In this embodiment, adjacent multiple strands follow the same coil pitch. However, even with coils touching each other, the pitch can be greater than a single strand arrangement (e.g., as shown in FIG. 10). This construction (i.e., larger pitch with coils touching) can be beneficial to reduce "play" in the coil; that is, as the flexible drill bit 5 starts drilling into bone, the helical coil 60 will more quickly respond in carrying a portion of the torque.

Figure 12:
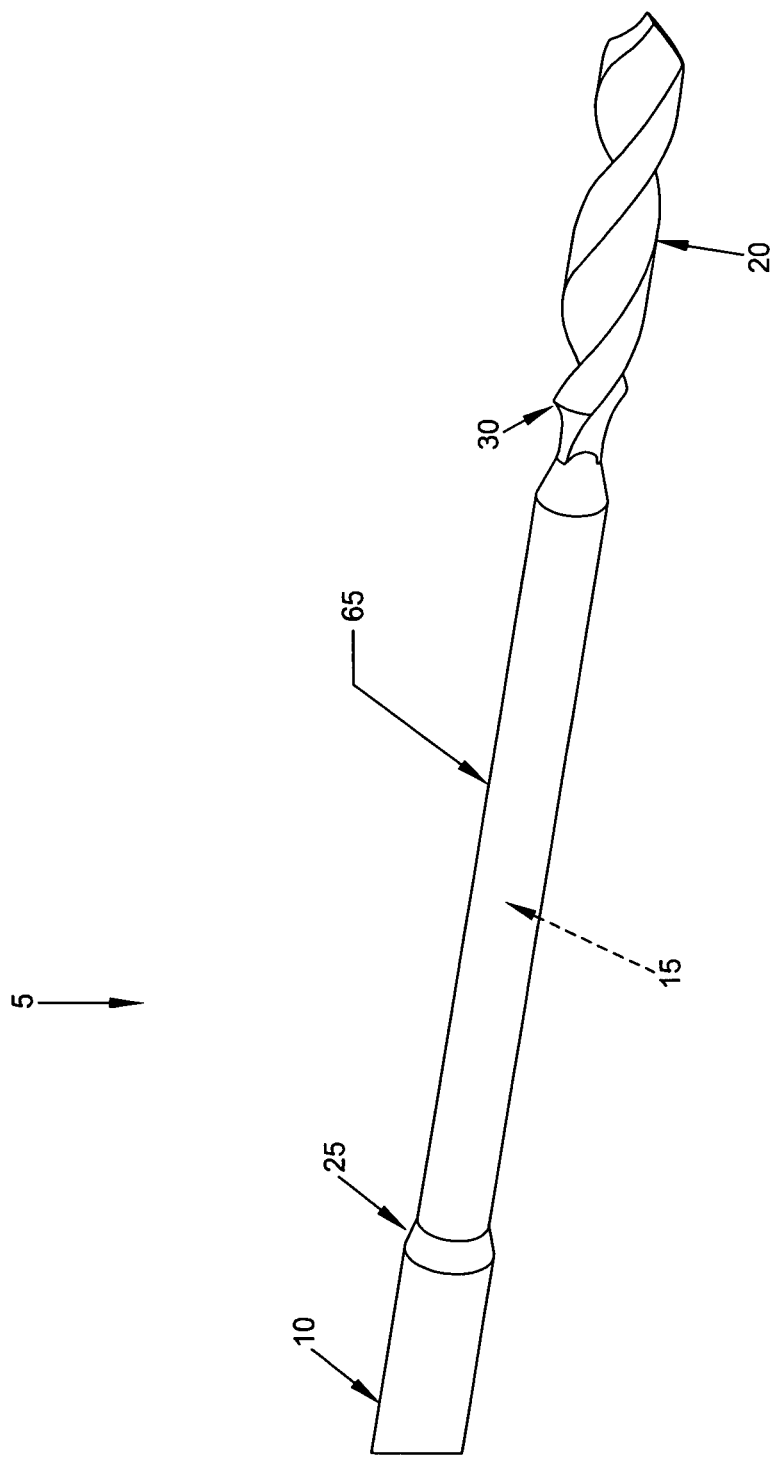
FIG. 12 is a schematic view showing the flexible drill bit of FIG. 1 with an over-molded sheath disposed over a portion of the flexible drill bit.

In another embodiment, and looking now at FIG. 12, an over-molded sheath 65 may be positioned over reduced diameter shaft portion 15 of flexible drill bit 5. Over-molded sheath 65 provides reduced friction (e.g., with curved drill guide 35 and/or bone 40) and increased diameter to reduced diameter shaft portion 15 of flexible drill bit 5, while still enabling bending of the reduced diameter shaft portion 15 of flexible drill bit 5. Over-molded sheath 65 may comprise a polymer such as Nylon or polytetrafluoroethylene (PTFE). Over-molded sheath 65 may be over-molded onto reduced diameter shaft portion 15 by injection molding or by diameter reduction (e.g., by shrinking or melting over-molded sheath 65 onto reduced diameter shaft portion 15).

Figure 13:
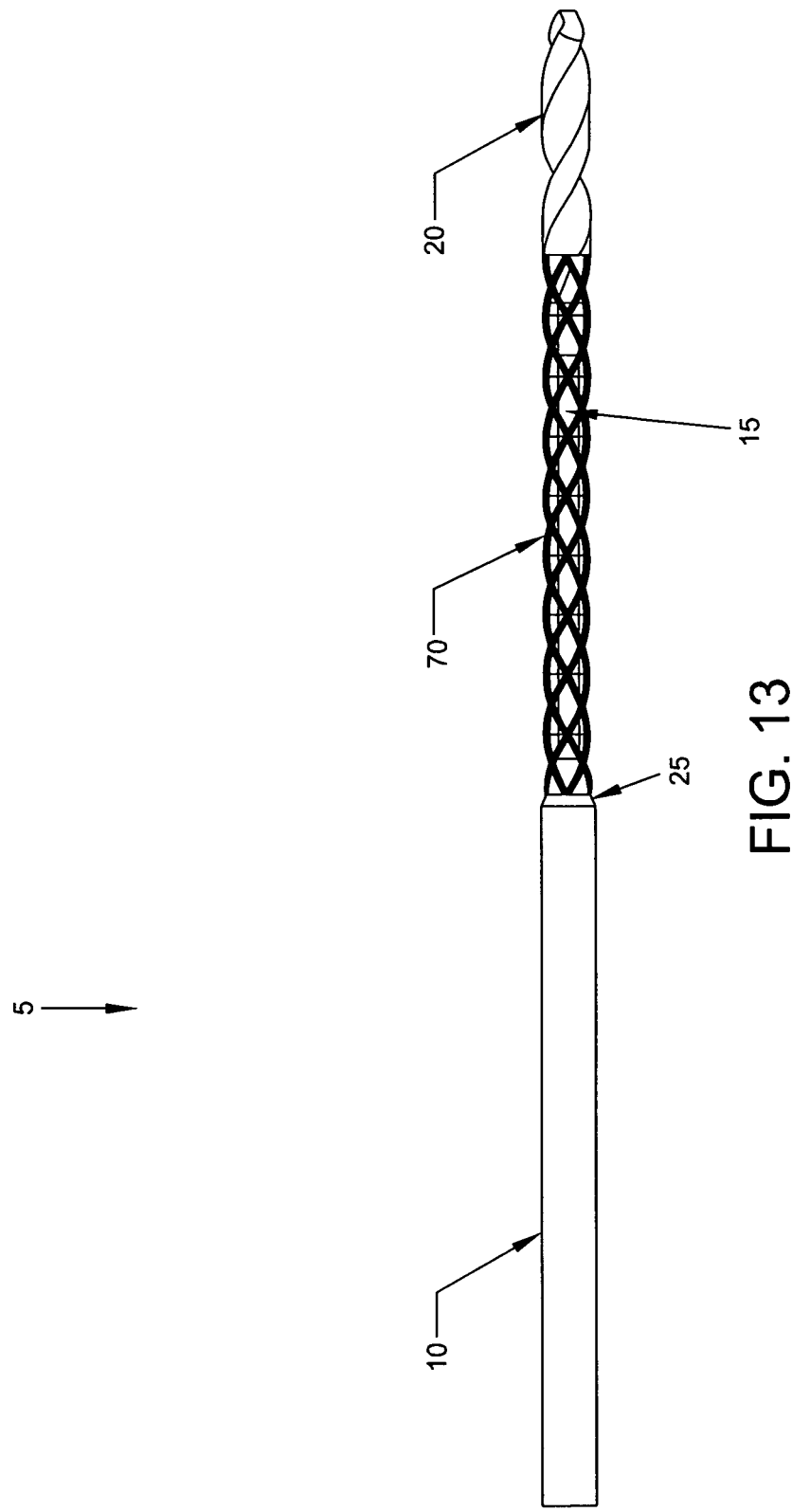
FIG. 13 is a schematic view showing the flexible drill bit of FIG. 1 with a metal braid or mesh disposed over a portion of the flexible drill bit.

In another embodiment, and looking now at FIG. 13, a braid or mesh 70 (preferably but not necessarily formed out of metal) may be positioned over reduced diameter shaft portion 15 of flexible drill bit 5. Metal braid or mesh 70 provides torsional strength and increased diameter to reduced diameter shaft portion 15 of flexible drill bit 5, while still enabling bending/flexing of reduced diameter shaft portion 15 of flexible drill bit 5. Metal braid or mesh 70 may comprise a material such as stainless steel or Nitinol. It may comprise wire having a rectangular cross-section. Metal braid or mesh 70 may be attached to reduced diameter shaft portion 15 of flexible drill bit 5 by attaching one or both of its ends to the reduced diameter shaft portion, or by attaching an intermediate portion of metal braid or mesh 70 to reduced diameter shaft portion 15, or both (e.g., by welding, adhesive, etc.). Alternatively, or additionally, a polymer (e.g., Pebax) may be heated and melted into the metal braid or mesh 70 so as to create a solid structure atop reduced diameter shaft portion 15. This polymer can provide a lower friction surface than the metal braid or mesh 70 alone, and can provide some torque transmission as well.

Figure 14:
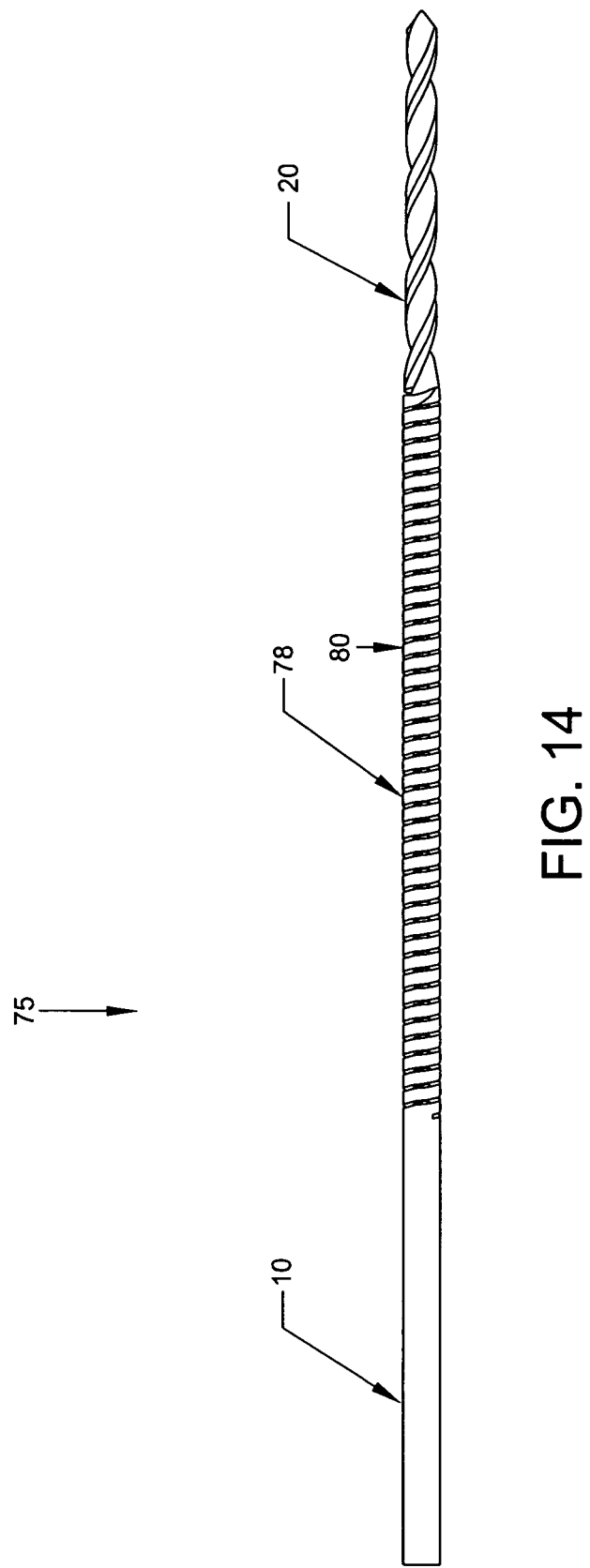
FIG. 14 is a schematic view showing another form of flexible drill bit formed in accordance with the present invention.
Figure 29:
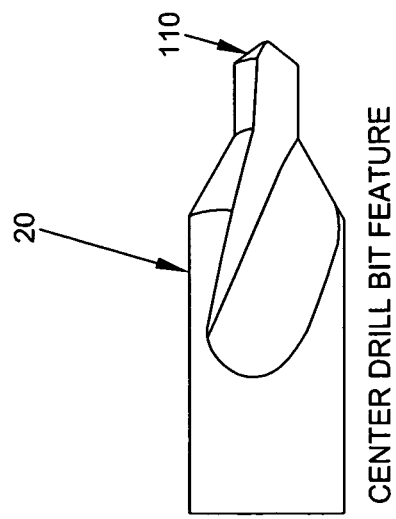
FIGS. 28-32 are schematic views showing various forms of cutting tips which may be used with the flexible drill bit of the present invention.
Figure 28:
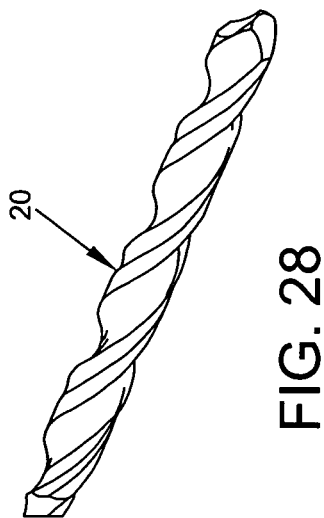
Figure 30:
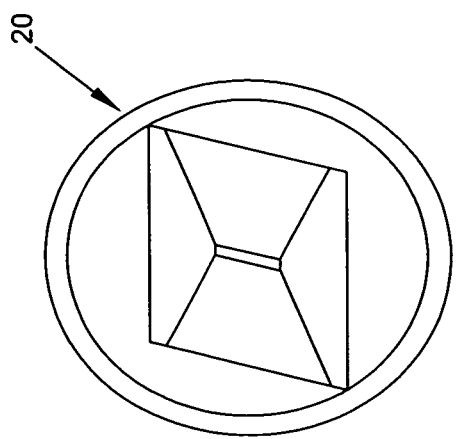
Figure 31:
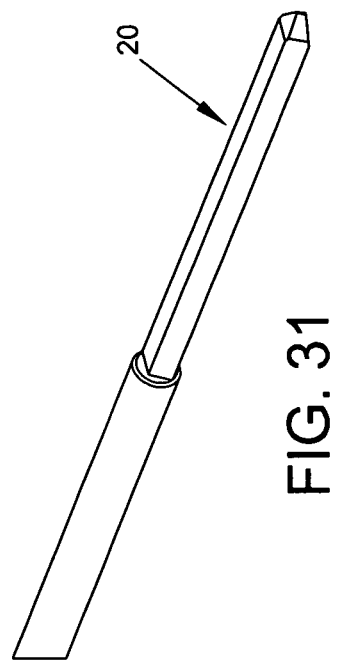

Looking next at FIG. 14, there is shown a flexible drill bit 75 which is similar to the flexible drill bit 5 shown in FIG. 1, however, instead of providing a reduced diameter shaft portion (e.g., the aforementioned reduced diameter shaft portion 15) between the full diameter shaft portion (e.g., the aforementioned full diameter shaft portion 10) and the fluted cutting tip portion (e.g., the aforementioned fluted cutting tip portion 20) in order to create the desired flexibility in the drill bit, the full diameter shaft portion extends all the way to the fluted cutting tip portion and portions of material are removed from the full diameter shaft portion so as to create the desired flexibility in the drill bit while providing greater torque carrying strength as compared to simply a reduced diameter shaft portion 15.

More particularly, in this embodiment, and looking now at FIG. 14, flexible drill bit 75 comprises a full diameter shaft portion 10 and a fluted cutting tip portion 20, with full diameter shaft portion 10 and fluted cutting tip portion 20 being formed integral with one another (i.e., a "unibody" design). In order to render the distal end 78 of full diameter shaft portion 10 flexible, material is removed from the full diameter shaft portion so as to create a flexible portion along the full diameter shaft portion of the drill bit. The material is removed in a pattern which enhances shaft flexibility but minimizes the reduction of torque transmission. In one preferred form of the invention, the material is removed in a spiral pattern as shown at 80 in FIG. 14 and may be accomplished by laser cutting, electrical discharge machining (i.e., EDM), machining, grinding or other means. For a clockwise rotating flexible drill bit 5, spiral cuts 80 are preferably formed in a clockwise pattern (when viewed from proximal to distal direction), but may also be formed in a counter-clockwise pattern.

Material may also be removed from full diameter shaft portion 10 in other patterns so as to create a flexible, yet high torque transmitting, portion along the shaft of the drill bit. By way of example but not limitation, and looking now at FIG. 15, a series of transverse slots 85 (instead of the spiral cuts 80 shown in FIG. 14) may be cut into the shaft, with the slots preferably following a spiral or other geometric pattern. Transverse slots 85 may be formed with various configurations. FIGS. 16-19 show one way of configuring transverse slots 85. FIGS. 20-23 show another way of configuring transverse slots 85. Still other ways of configuring transverse slots 85 will be apparent to those skilled in the art in view of the present disclosure.

In this embodiment if the invention, flexible drill bit 75 may comprise a material such as stainless steel or Nitinol.

Flexible Drill Bit Having a Multi-Body Construction

In another embodiment of the present invention, portions of the flexible drill bit (e.g., the cutting tip) may comprise separate components which are connected to the remaining portions of the flexible drill bit (e.g., the solid shaft) in order to provide a flexible drill bit having a multi-body construction.

More particularly, and looking now at FIGS. 24 and 25, there is a shown a flexible drill bit 90 comprising two components (i.e., full diameter shaft portion 10 and fluted cutting tip portion 20) which are connected together so as to form a flexible drill bit having three sections, i.e., a distal cutting tip, a proximal shaft and an intermediate flexible region. In this embodiment of the invention, fluted cutting tip portion 20 comprises an elongated solid shaft 95 which is received within a lumen 100 formed in full diameter shaft portion 10 and then secured therein (e.g., by welding, adhesive bond, swaging, etc. or a combination thereof or other means well known in the art). Full diameter shaft portion 10 is preferably secured to fluted cutting tip portion 20 at the distal end of full diameter shaft portion 10, e.g., at 102. Flexible drill bit 90 may comprise additional points of securement between full diameter shaft portion 10 and fluted cutting tip portion 20 (e.g., proximal of the intermediate flexible region, such as at 103). The drill bit is rendered flexible by removing material from full diameter shaft portion 10, e.g., such as by forming spiral cuts 80 in full diameter shaft portion 10. Although spiral cuts 80 are shown in FIGS. 24 and 25 as being formed in a clockwise pattern (when viewed from proximal to distal direction), they preferably would be formed in a counter-clockwise pattern when used with a clockwise-rotating drill (when viewed from proximal to distal) so that the spiral cuts would tend to tighten down on the elongated solid shaft 95 during drilling. Alternatively, and looking now at FIGS. 26 and 27, the material may be removed as an interrupted spiral cut 105 so as to provide the desired flexibility to the drill bit. In one preferred form of this embodiment, the cuts are interrupted segment lengths of less an 120 degrees around the perimeter, have a opening—or width—which is less than the pitch distance (i.e., longitudinal distance between adjacent cuts), and have a gap between laser cuts which is approximately equal to the pitch distance. In one preferred form of this embodiment, the cuts have a slight angle relative to perpendicular to the longitudinal axis of the flexible drill bit 90.

Depending on the location(s) of securement between full diameter shaft portion 10 and fluted cutting tip portion 20 (e.g., at securement point 102, securement point 103, etc.), the torque may be transmitted through the full diameter shaft portion 10 (distal securement only), through solid shaft 95 of fluted cutting tip portion 20 (proximal securement only) or shared between the two (both the proximal and distal securements).

Cutting Tip Constructions

Figure 32:
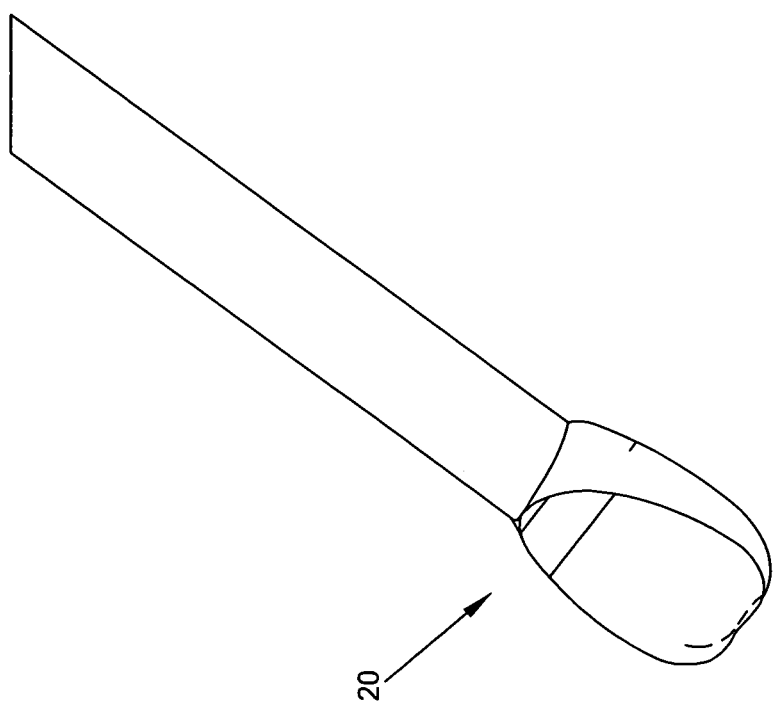

Looking now at FIGS. 28-32, there are shown various shapes and designs of cutting tips which may be used in accordance with the present invention, e.g., a fluted cutting tip (FIG. 28), a fluted cutting tip with a centering feature 110 similar to a center drill bit (FIG. 29), a diamond shape (FIGS. 30 and 31) or a forged or flattened tip (FIG. 32). In the cutting tip embodiment of a fluted cutting tip (e.g., FIG. 28), the inclusive angle at the tip may be approximately 30-120 degrees, is more preferably approximately 60-90 degrees, and is most preferably approximately 70 degrees.

Helical Structures

In the foregoing disclosure, various constructions are provided in which the flexible drill bit comprises a helical structure. By way of example but not limitation, a helical coil 60 is mounted over reduced diameter shaft portion 15 (FIGS. 10 and 11), a helical groove is formed in full diameter shaft portion 10 (FIGS. 14 and 24-27), etc. These constructions are provided in order to maximize the flexibility of the drill bit while minimizing reduction of torque transmission through the drill bit. In this respect it will be appreciated that the configuration of the helical structure (i.e., the direction of the spiral) is preferably related to the direction of the applied torque, in order to maintain maximum torque transmission through the drill bit. However, the relationship of these may vary depending on the specific construction of the drill bit.

In the embodiment of a helical coil mounted over a reduced diameter shaft portion (FIGS. 10 and 11), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. Such an inverse relationship between the direction of the applied torque and the direction of the spiral will ensure that any deformation of the helical coil from the applied torque will cause the helical coil to tighten, whereby to preserve torque transmission through the helical coil.

In the embodiment of a helical groove formed in a full diameter shaft portion (FIGS. 14 and 24-27), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. The appropriate relationship between the direction of the applied torque and the direction of the spiral will maximize torque transmission while maintaining drill bit flexibility.

General Construction

The flexible drill bit may comprise Nitinol or stainless steel or any other material which is flexible enough to bend into a curved state, and strong enough to transmit the torsional forces required for drilling into bone.

The entire shaft or portions of the shaft can be coated to reduce friction (e.g., with curved drill guide 35 and/or bone 40).

Modifications

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for forming a hole in a material, the method comprising:
   providing a flexible drilling system, the flexible drilling system comprising an angled drill guide and a flexible drill bit;
   wherein the angled drill guide comprises a proximal end, a distal end and a lumen extending between the proximal end and the distal end, wherein the lumen comprises a curve having a length;
   wherein the flexible drill bit comprises:
      a proximal shaft portion configured to be connected to a source of turning, the proximal shaft portion having a diameter sized to be received in the lumen of the drill guide;
      a distal cutting tip portion for boring into a material, the distal cutting tip portion having a diameter; and
      an intermediate shaft portion extending between the proximal shaft portion and the distal cutting tip portion, the intermediate shaft portion having a diameter;
      wherein the distal cutting tip portion, the intermediate shaft portion and the proximal shaft portion are formed out of a single piece of material so as to form a unibody construction;

wherein the diameter of the intermediate shaft portion is smaller than the diameter of the distal cutting tip portion; and wherein the diameter of the intermediate shaft portion is approximately 20%-40% smaller than the diameter of the proximal shaft portion, the intermediate shaft portion having a length that is longer than the length of the curve of the lumen of the angled drill guide;

wherein a gap is formed between a side wall of the lumen of the angled drill guide and the intermediate shaft portion of the flexible drill bit when the intermediate shaft portion of the flexible drill bit is received in the lumen of the angled drill guide, and further wherein the gap is sized so that when the distal end of the angled drill guide is set perpendicularly to the material, the distal cutting tip portion of the flexible drill bit will enter the material at a non-perpendicular angle;

advancing the distal cutting tip portion of the flexible drill bit through the lumen of the angled drill guide;

contacting the material with the distal cutting tip portion of the flexible drill bit; and turning the flexible drill bit so as to form a hole in the material.

2. A method according to claim 1 wherein the proximal shaft portion is substantially rigid.

3. A method according to claim 1 wherein the source of turning is a drill.

4. A method according to claim 1 wherein the material is bone.

5. A method according to claim 1 wherein the lumen of the angled drill guide has a radius of curvature of approximately 1.25 inches.

6. A method according to claim 1 wherein the intermediate shaft portion has sufficient torsional strength to transmit at least two inch-pounds of torque.

7. A method according to claim 1 wherein a transition area is formed between the intermediate shaft portion and the proximal shaft portion.

8. A method according to claim 1 wherein the hole formed in the material has a depth, and further wherein the depth of the hole formed in the bone is deeper than the length of the distal cutting tip portion.

9. A method according to claim 1 wherein the distal cutting tip portion is fluted.

10. A method according to claim 1 wherein a transition area is formed between the intermediate shaft portion and the distal cutting tip portion, wherein the transition area tapers from the distal cutting tip portion to the intermediate shaft portion.

11. A method according to claim 1 wherein the length of the distal cutting tip portion is approximately six times greater than the diameter of the distal cutting tip portion.

12. A method according to claim 1 wherein the curve of the lumen of the angled drill guide forms an inside of the curve and an outside of the curve, wherein while the flexible drill bit is turning to form the hole in the material, a first portion of the intermediate shaft portion engages the outside of the curve of the lumen of the angled drill guide and a second portion of the intermediate shaft portion engages the inside of the curve of the lumen of the angled drill guide.

13. A method according to claim 1 wherein the diameter of the distal cutting tip portion is smaller than the diameter of the proximal shaft portion.

14. A method for forming a hole in a material, the method comprising:

providing a flexible drilling system, the flexible drilling system comprising an angled drill guide and a flexible drill bit;

wherein the angled drill guide comprises a proximal end, a distal end and a lumen extending between the proximal end and the distal end, wherein the lumen comprises a curve having a length;

wherein the flexible drill bit comprises:

a proximal shaft portion configured to be connected to a source of turning, the proximal shaft portion having a diameter sized to be received in the lumen of the drill guide;

a distal cutting tip portion for boring into a material, the distal cutting tip portion having a diameter; and an intermediate shaft portion extending between the proximal shaft portion and the distal cutting tip portion, the intermediate shaft portion having a diameter;

wherein the distal cutting tip portion, the intermediate shaft portion and the proximal shaft portion are formed out of a single piece of material so as to form a unibody construction;

wherein the diameter of the intermediate shaft portion is smaller than the diameter of the distal cutting tip portion; and wherein the diameter of the intermediate shaft portion is approximately 20%-40% smaller than the inner diameter of the lumen of the angled drill guide, the intermediate shaft portion having a length that is longer than the length of the curve of the lumen of the angled drill guide;

wherein a gap is formed between a side wall of the lumen of the angled drill guide and the intermediate shaft portion of the flexible drill bit when the intermediate shaft portion of the flexible drill bit is received in the lumen of the angled drill guide, and further wherein the gap is sized so that when the distal end of the angled drill guide is set perpendicularly to the material, the distal cutting tip portion of the flexible drill bit will enter the material at a non-perpendicular angle;

advancing the distal cutting tip portion of the flexible drill bit through the curve in the lumen of the angled drill guide;

contacting the material with the distal cutting tip portion of the flexible drill bit; and turning the flexible drill bit so as to form a hole in the material.

15. A method according to claim 14 wherein the distal cutting tip portion is fluted.

16. A method according to claim 14 wherein the proximal shaft portion is substantially rigid.

17. A method according to claim 14 wherein the source of turning is a drill.

18. A method according to claim 14 wherein the material is bone.

19. A method according to claim 14 wherein the lumen of the angled drill guide has a radius of curvature of approximately 1.25 inches.

20. A method according to claim 14 wherein the intermediate shaft portion has sufficient torsional strength to transmit at least two inch-pounds of torque.

21. A method according to claim 14 wherein a transition area is formed between the intermediate shaft portion and the proximal shaft portion.

22. A method according to claim 14 wherein the hole formed in the material has a depth, and further wherein the depth of the hole formed in the bone is deeper than the length of the distal cutting tip portion.

23. A method according to claim 14 wherein a transition area is formed between the intermediate shaft portion and the distal cutting tip portion, wherein the transition area tapers from the distal cutting tip portion to the intermediate shaft portion.

24. A method according to claim 14 wherein the length of the distal cutting tip portion is approximately six times greater than the diameter of the distal cutting tip portion.

25. A method according to claim 14 wherein the diameter of the distal cutting tip portion is smaller than the diameter of the proximal shaft portion.

26. A method for forming a hole in a material, the method comprising:
providing a flexible drilling system, the flexible drilling system comprising an angled drill guide and a flexible drill bit;
wherein the angled drill guide comprises a proximal end, a distal end and a lumen extending between the proximal end and the distal end;
wherein the flexible drill bit comprises:
a proximal shaft portion configured to be connected to a source of turning, the proximal shaft portion having a diameter sized to be received in the lumen of the drill guide;
a distal cutting tip portion for boring into a material, the distal cutting tip portion having a diameter; and
an intermediate shaft portion extending between the proximal shaft portion and the distal cutting tip portion, the intermediate shaft portion having a diameter;
wherein the distal cutting tip portion and the intermediate shaft portion are formed integral with one another so as to form a unibody construction;
wherein the distal cutting tip portion is more rigid than the intermediate shaft portion;
wherein the diameter of the intermediate shaft portion is smaller than the diameter of the distal cutting tip portion;
wherein the diameter of the intermediate shaft portion is smaller than the diameter of the proximal shaft portion;
wherein a gap is formed between a side wall of the lumen of the angled drill guide and the intermediate shaft portion of the flexible drill bit when the intermediate shaft portion of the flexible drill bit is received in the lumen of the angled drill guide, and further wherein the gap is sized so that when the distal end of the angled drill guide is set perpendicularly to the material, the distal cutting tip portion of the flexible drill bit will enter the material at a non-perpendicular angle;
advancing the distal cutting tip portion of the flexible drill bit through the lumen of the angled drill guide;
entering the material with the distal cutting tip portion of the flexible drill bit, wherein the distal cutting tip portion enters the material at a non-perpendicular angle; and
turning the flexible drill bit so as to form a hole in the material.

27. A method according to claim 26 wherein the distal cutting tip portion is fluted.

28. A method according to claim 26 wherein the proximal shaft portion is substantially rigid.

29. A method according to claim 26 wherein the source of turning is a drill.

30. A method according to claim 26 wherein the material is bone.

31. A method according to claim 26 wherein the lumen of the angled drill guide has a radius of curvature of approximately 1.25 inches.

32. A method according to claim 26 wherein the intermediate shaft portion has sufficient torsional strength to transmit at least two inch-pounds of torque.

33. A method according to claim 26 wherein the proximal shaft portion, the intermediate shaft portion and the distal cutting tip portion are formed integral with one another.

34. A method according to claim 26 wherein a transition area is formed between the intermediate shaft portion and the proximal shaft portion.

35. A method according to claim 26 wherein the hole formed in the material has a depth, and further wherein the depth of the hole formed in the bone is deeper than the length of the distal cutting tip portion.

36. A method according to claim 26 wherein a transition area is formed between the intermediate shaft portion and the distal cutting tip portion, wherein the transition area tapers from the distal cutting tip portion to the intermediate shaft portion.

37. A method according to claim 26 wherein the length of the distal cutting tip portion is approximately six times greater than the diameter of the distal cutting tip portion.

38. A method according to claim 26 wherein the diameter of the distal cutting tip portion is smaller than the diameter of the proximal shaft portion.

39. A method according to claim 1 further comprising inserting a suture anchor in the hole formed in the material.

40. A method according to claim 14 further comprising inserting a suture anchor in the hole formed in the material.

* * * * *